(12) United States Patent
Spielberg et al.

(10) Patent No.: US 10,596,266 B2
(45) Date of Patent: Mar. 24, 2020

(54) STABLE LIQUID FORMULATIONS FOR PHARMACEUTICALS AND SUPPLEMENTS COMPRISING AN HERBAL MIXTURE

(71) Applicants: Max Spielberg, Beverly Hills, CA (US); David Johnson, Beverly Hills, CA (US)

(72) Inventors: Max Spielberg, Beverly Hills, CA (US); David Johnson, Beverly Hills, CA (US)

( * ) Notice: Subject to any disclaimer, the term of this patent is extended or adjusted under 35 U.S.C. 154(b) by 25 days.

(21) Appl. No.: 15/912,785

(22) Filed: Mar. 6, 2018

(65) Prior Publication Data

US 2019/0125881 A1 May 2, 2019

Related U.S. Application Data

(60) Provisional application No. 62/580,648, filed on Nov. 2, 2017.

(51) Int. Cl.
| | |
|---|---|
| *A61K 36/00* | (2006.01) |
| *A61K 47/46* | (2006.01) |
| *A61K 9/00* | (2006.01) |
| *A61K 36/88* | (2006.01) |
| *A61K 35/644* | (2015.01) |
| *A61K 36/736* | (2006.01) |
| *A61K 36/35* | (2006.01) |
| *A61P 11/14* | (2006.01) |
| *A61K 36/235* | (2006.01) |
| *A61K 47/26* | (2006.01) |
| *A61K 36/9068* | (2006.01) |
| *A61K 47/12* | (2006.01) |
| *A61K 36/9066* | (2006.01) |
| *A61K 36/074* | (2006.01) |

(52) U.S. Cl.
CPC ........... *A61K 47/46* (2013.01); *A61K 9/0095* (2013.01); *A61K 35/644* (2013.01); *A61K 36/074* (2013.01); *A61K 36/235* (2013.01); *A61K 36/35* (2013.01); *A61K 36/736* (2013.01); *A61K 36/88* (2013.01); *A61K 36/9066* (2013.01); *A61K 36/9068* (2013.01); *A61K 47/12* (2013.01); *A61K 47/26* (2013.01); *A61P 11/14* (2018.01)

(58) Field of Classification Search
CPC .................................................... A61K 36/00
See application file for complete search history.

(56) References Cited

U.S. PATENT DOCUMENTS

2015/0132271 A1\* 5/2015 Chang ................ A61K 31/4709
424/93.51

\* cited by examiner

*Primary Examiner* — Rosanne Kosson
(74) *Attorney, Agent, or Firm* — David W. Barman

(57) ABSTRACT

A liquid composition comprising: a primary component being an Active Pharmaceutical Ingredient (API), a nutritional supplement, or combinations thereof: a base; and a preservative blend is provided along with a method of making said composition.

3 Claims, No Drawings

STABLE LIQUID FORMULATIONS FOR PHARMACEUTICALS AND SUPPLEMENTS COMPRISING AN HERBAL MIXTURE

INDEX TO RELATED APPLICATIONS

This application is a non-provisional of, and claims benefit to U.S. Provisional Patent Application Ser. No. 62/580,648 filed Nov. 2, 2017 the disclosure of which is incorporated herein by reference in its entirety.

BACKGROUND OF THE INVENTION

A significant area of concern in formulations of liquid pharmaceutical and supplemental products relate to stability and shelf life. It is well-known that stability must allow sufficient time for shipping and ultimate consumer purchase. The formulation scientist often encounters various limitations in the suitability of stabilizing components. There is a need for a stabilizing preservative blend with broad suitability. The present invention addresses this need.

SUMMARY OF THE INVENTION

The present invention relates to novel stabilization of liquid pharmaceutical and nutritional supplements.

In one embodiment, the present invention is a liquid composition comprising:
a primary component being an Active Pharmaceutical Ingredient (API), a nutritional supplement, or combinations thereof:
a base;
a preservative blend comprising either, Organic Cultured Dextrose, Organic Elderberry (16:1 Fruit Powder)
Organic Compliant Citric Acid
Organic Turmeric Root Powder
Organic Fennel Seed Powder
Organic Ginger Root, in a ratio of 1:0.8-1.0:0.55-0.65:0.40-0.54:0.05-0.09:0.05-0.09 or
Organic Cultured Dextrose
Organic Elderberry (16:1 Fruit Powder)
Organic Compliant Citric Acid
Organic Echinacea Purpurea Herb (6:1), in a ratio of 1:0.60-0.70:0.55-0.65:0.35-0.44.

In one embodiment, the present invention provides the preservative blend is 2-5% w/w of the composition.

In one embodiment, the present invention is a liquid composition consisting of:
a primary component being an Active Pharmaceutical Ingredient (API), a nutritional supplement, or combinations thereof:
a base;
a preservative blend comprising either, Organic Cultured Dextrose, Organic Elderberry (16:1 Fruit Powder)
Organic Compliant Citric Acid
Organic Turmeric Root Powder
Organic Fennel Seed Powder
Organic Ginger Root, in a ratio of 1:0.8-1.0:0.55-0.65:0.40-0.54:0.05-0.09:0.05-0.09 or
Organic Cultured Dextrose
Organic Elderberry (16:1 Fruit Powder)
Organic Compliant Citric Acid
Organic Echinacea Purpurea Herb (6:1), in a ratio of 1:0.60-0.70:0.55-0.65:0.35-0.44.

In one embodiment, the present invention is a method of preparing a liquid composition as described herein comprising the steps of:

Providing components of a preservative blend comprising either Organic Compliant Citric Acid
Organic Turmeric Root Powder
Organic Fennel Seed Powder
Organic Ginger Root, or
Organic Cultured Dextrose
Organic Elderberry (16:1 Fruit Powder)
Organic Compliant Citric Acid
Organic Echinacea Purpurea Herb (6:1),
and combing them into an herbal pre-mix, blend into a small amount of the base and heat between 180-200 degrees Fahrenheit, to create the pre-mix containing the herbal ingredients;
combining the pre-mix and mix with the remainder of the agave/honey (the majority of the formula), which was heated to about 100° F. degrees until the pre-mix is homogenous and becomes one product;
cooling the combined mixture to room temperature and introduce flavors once at room temperature;
placing the combined cooled room temperature product containing flavors (pre-mix and remainder of formula); and
mixing to form a uniform composition.

DETAILED DESCRIPTION OF THE PREFERRED EMBODIMENT

The present invention relates to novel stabilization of liquid pharmaceutical and nutritional supplements.

Although the examples provided herein are nutritional supplements, it is contemplated that any Active Pharmaceutical Ingredient (API) or nutritional supplement ingredient is formulated according to the invention disclosed herein and will produce a stable composition with desired shelf life.

In one embodiment, the present invention includes the process of blending an herbal pre-mix with a small amount of the base (in this case, agave or honey) and heating at a high temperature (about 180-200 degrees Fahrenheit), subsequently mixing the pre-mix with the remainder of the formula, which has been heated to be at a lower temperature (about 100° F.). By heating the pre-mix and base and the remainder of base separately and at different temperatures, the novel process will reduce the froth and prevent flavor changes. This is the first time such a system has been used.

In one embodiment, the present invention includes using approximately 80-90% solid base (in this case, 84% solid agave or honey depending) with combination of cultured dextrose and citric acid in order to not have to put in a non-organic, synthetic preservative systems. This allows the present invention to have a certified organic base without any synthetic preservative systems. This is the first time this combination of high percentage solid base, citric acid and cultured dextrose has been used.

In formulations practice, it is known that often two or more preservatives are provided. Sometimes they are provided for specific preserving characteristics. However, there are preservative systems that are utilized with various components having beneficial synergistic affects even thought the exact mechanism of the beneficial synergistic affects is not clearly understood. This is true in the present formulation whereby a synergistic system has been discovered, demonstrated effective, yet is operating in a mechanism not fully understood.

In the present invention, particular ratios have been discovered whereby a plurality of components in the ratios herein, provide the desired effect.

Initial formulas were exactly the same, except the agave was around 60-70% solid and they did not have cultured dextrose. These formulas did not have an effective preservation system, and failed stability testing.

Manufacture

In one embodiment, the present invention is performed using the following steps:

Providing organic herbal extracts and combing them into an herbal pre-mix, blend into a small amount of the base (here, agave or honey depending) and heat between 180-200 degrees Fahrenheit, to create the pre-mix containing the herbal ingredients.

Although the examples demonstrate Agave and Honey as the base, the term "base" as used herein includes components having similar viscosities and characteristics including, but not limited to tapioca syrups, fruit syrups, maple syrups, elderberry syrup, combinations of bases, and the like.

As is known, Agave will break down at 320° F. and will even begin to change at 210° F., therefore 180-200° F. is one ideal temperature range to extract the herbal ingredients into the agave/honey without hurting them or the agave/honey. The present invention contemplates temperature for other types of syrups with similar consistencies at similar temperatures.

Combining the pre-mix and mix with the remainder of the agave/honey (the majority of the formula), which was heated to about 100° F. degrees until the pre-mix is homogenous and becomes one product.

Cooling the combined mixture to room temperature and introduce flavors once at room temperature.

Placing the combined cooled room temperature product containing flavors (pre-mix and remainder of formula) and mix into a mixer.

It has been discovered that separately handling the pre-mix and remainder of formula separately, prevents flavor changes and froth. This then helps reduce and prevent sheer and flavor changes as the sheer and flavor changes are caused by warming at a high temperature. Heating the herbal pre-mix is necessary to blend the herbal ingredients into the base.

Sample Formulations:

| FORMULA 1 - AGAVE COUGH SYRUP | |
|---|---|
| Organic Agave Syrup | 4.6 g |
| Organic Acerola (containing 34% naturally occurring Vitamin C) | 29 mg |
| Proprietary Blend: Organic Elderberry Fruit Powder (16:1), Organic Fennel Extract, Organic Turmeric, Organic Ginger Root. | 27 mg |

| FORMULA 2 - HONEY COUGH SYRUP | |
|---|---|
| Organic Honey | 6.3 g |
| Organic Echinacea | 15 mg |
| Organic Elderberry Fruit Powder (16:1) | 25 mg |
| Organic Acerola (containing 34% naturally occurring Vitamin C) | 75 mg |

| FORMULA 3 - AGAVE TEETHING SYRUP | |
|---|---|
| Organic Agave Syrup | 4.6 g |
| Organic Acerola (containing 34% naturally occurring Vitamin C) | 29 mg |
| Proprietary Blend: Organic Elderberry Fruit Powder (16:1), Organic Turmeric, Organic Reishi Mushroom. | 25 mg |

Agave Cough Syrup—Percentage Composition

| Formulation: | Mg per serving: | Percentage |
|---|---|---|
| Organic Agave Syrup | 2,894.28 | 96.4761172% |
| Organic Acerola (34% Vitamin C) | 30.88 | 1.0294118% |
| Organic Cultured Dextrose | 24.26 | 0.8085000% |
| Organic Elderberry (16:1 Fruit Powder) | 21.00 | 0.7000000% |
| Organic Compliant Citric Acid | 14.45 | 0.4816700% |
| Organic Cherry Flavor | 11.13 | 0.3709677% |
| Organic Reishi Mushroom Powder | 2.00 | 0.0666667% |
| Organic Turmeric Root Powder | 2.00 | 100.0666667% |
| Total: | 3,000.00 | 100.000000% |

Honey Cough Syrup—Percentage Composition

| Formulation: | Mg per serving: | Percentage |
|---|---|---|
| Organic Honey | 4,530.88 | 90.6176871% |
| Purified Water | 285.71 | 5.7142857% |
| Organic Acerola (34% Vitamin C) | 78.75 | 1.5750000% |
| Organic Cultured Dextrose | 40.43 | 0.8085000% |
| Organic Elderberry (16:1 Fruit Powder) | 25.00 | 0.5000000% |
| Organic Compliant Citric Acid | 24.08 | 0.4816700% |
| Organic Echinacea Purpurea Herb (6:1) | 15.00 | 0.3000000% |
| Organic Compliant Lemon Flavor | 0.14 | 0.0028571% |
| Total: | 5,000.00 | 100.000000% |

Agave Teething Syrup

| Formulation: | Mg per serving: | Percentage |
|---|---|---|
| Organic *Agave* Syrup | 2,892.28 | 96.4094505% |
| Organic Acerola (34% Vitamin C) | 30.88 | 1.0294118% |
| Organic Cultured Dextrose | 24.26 | 0.8085000% |
| Organic Elderberry (16:1 Fruit Powder) | 21.00 | 0.7000000% |
| Organic Compliant Citric Acid | 14.45 | 0.4816700% |
| Organic Cherry Flavor | 11.13 | 0.3709677% |
| Organic Turmeric Root Powder | 2.00 | 0.0666667% |
| Organic Fennel Seed Powder | 2.00 | 0.0666667% |
| Organic Ginger Root | 2.00 | 0.0666667% |
| Total: | 3,000.00 | 100.000000% |

Preservative Efficay Testing
USP Preservative Efficay
Agave Cough Syrup

| Test Organisms | Inoculum Level (CFU/g) | ATCC Number |
|---|---|---|
| *Escherichia coli* | $4.9 \times 10^5$ | 8739 |
| *Pseudomonas aeruginosa* | $6.0 \times 10^5$ | 9027 |
| *Staphylococcus aureus* | $5.0 \times 10^5$ | 6538 |
| *Candida albicans* | $2.6 \times 10^5$ | 10231 |
| *Aspergillus* (niger) *brasiliensis* | $3.1 \times 10^5$ | 16404 |

Method

The sample was challenged against the five individual microorganisms listed above following the USP <51> guidelines. Pure culture challenge yields specific data on each microorganism employed in the study.

The sample was initially tested for aerobic bacteria, yeast, and mold following the USP <51> guidelines. This initial screen is imperative to ensure the product does not contain any microorganisms prior to beginning the inoculations. No organisms were found in the sample during the initial screen.

Effectiveness Standards

Bacteria: Not less than 1.0 log reduction from the initial count at 14 days, and no increase from the 14 days' count at 28 days. Yeast and Molds: No increase from the initial calculated count at 14 and 28 days. Upon reinoculation, the same effectiveness standards apply.

| Test Interval | E. coli | P. aeruginosa | S. aureus | C. albicans | A. brasiliensis |
|---|---|---|---|---|---|
| 0 hours | $1.8 \times 10^5$ | $2.8 \times 10^4$ | $6.7 \times 10^5$ | $2.0 \times 10^3$ | $2.2 \times 10^4$ |
| 1 Week | 210 | 260 | 190 | <10 | $2.2 \times 10^3$ |
| 2 Weeks | <10 | <10 | <10 | <10 | 30 |
| 4 Weeks | <10 | <10 | <10 | <10 | <10 |

All results in the table are reported as CFU/g

Study Conclusion The sample has PASSED the test. The actual data collected from the study at each testing interval is listed on the following page.

USP Preservative Efficay
Honey Cough Syrup

| Test Organisms | Inoculum Level (CFU/g) | ATCC Number |
|---|---|---|
| Escherichia coli | $4.9 \times 10^5$ | 8739 |
| Pseudomonas aeruginosa | $6.0 \times 10^5$ | 9027 |
| Staphylococcus aureus | $5.0 \times 10^5$ | 6538 |
| Candida albicans | $2.6 \times 10^5$ | 10231 |
| Aspergillus (niger) brasiliensis | $3.1 \times 10^5$ | 16404 |

Method

The sample was challenged against the five individual microorganisms listed above following the USP <51> guidelines. Pure culture challenge yields specific data on each microorganism employed in the study.

The sample was initially tested for aerobic bacteria, yeast, and mold following the USP <51> guidelines. This initial screen is imperative to ensure the product does not contain any microorganisms prior to beginning the inoculations. No organisms were found in the sample during the initial screen.

Effectiveness Standards

Bacteria: Not less than 1.0 log reduction from the initial count at 14 days, and no increase from the 14 days' count at 28 days. Yeast and Molds: No increase from the initial calculated count at 14 and 28 days. Upon reinoculation, the same effectiveness standards apply.

Study Conclusion The sample has PASSED the test. The actual data collected from the study at each testing interval is listed on the following page.

USP Preservative Efficay
Agave Teething Syrup

| Test Organisms | Inoculum Level (CFU/g) | ATCC Number |
|---|---|---|
| Escherichia coli | $4.9 \times 10^5$ | 8739 |
| Pseudomonas aeruginosa | $6.0 \times 10^5$ | 9027 |
| Staphylococcus aureus | $5.0 \times 10^5$ | 6538 |
| Candida albicans | $2.6 \times 10^5$ | 10231 |
| Aspergillus (niger) brasiliensis | $3.1 \times 10^5$ | 16404 |

Method

The sample was challenged against the five individual microorganisms listed above following the USP <51> guidelines. Pure culture challenge yields specific data on each microorganism employed in the study.

The sample was initially tested for aerobic bacteria, yeast, and mold following the USP <51> guidelines. This initial screen is imperative to ensure the product does not contain any microorganisms prior to beginning the inoculations. No organisms were found in the sample during the initial screen.

Effectiveness Standards

Bacteria: Not less than 1.0 log reduction from the initial count at 14 days, and no increase from the 14 days' count at 28 days. Yeast and Molds: No increase from the initial calculated count at 14 and 28 days. Upon reinoculation, the same effectiveness standards apply.

| Test Interval | E. coli | P. aeruginosa | S. aureus | C. albicans | A. brasiliensis |
|---|---|---|---|---|---|
| 0 hours | $5.1 \times 10^5$ | $1.3 \times 10^5$ | $9.7 \times 10^5$ | $1.2 \times 10^5$ | $2.4 \times 10^4$ |
| 1 Week | 120 | 86 | $5.2 \times 10^4$ | 10 | $1.9 \times 10^4$ |
| 2 Weeks | <10 | <10 | <10 | <10 | $2.1 \times 10^3$ |
| 4 Weeks | <10 | <10 | <10 | <10 | 850 |

All results in the table are reported as CFU/g

| Test Interval | E. coli | P. aeruginosa | S. aureus | C. albicans | A. brasiliensis |
|---|---|---|---|---|---|
| 0 hours | $1.7 \times 10^5$ | $2.4 \times 10^4$ | $5.6 \times 10^5$ | $1.2 \times 10^3$ | $2.5 \times 10^4$ |
| 1 Week | 300 | 190 | 190 | <10 | $805 \times 10^3$ |
| 2 Weeks | <10 | <10 | <10 | <10 | 40 |
| 4 Weeks | <10 | <10 | <10 | <10 | <10 |

All results in the table are reported as CFU/g

Study Conclusion The sample has PASSED the test. The actual data collected from the study at each testing interval is listed on the following page.

The following represents the blend of ingredients demonstrative of one embodiment of the novel preservative system:

Preservative Blend 1
Organic Cultured Dextrose
Organic Elderberry (16:1 Fruit Powder)
Organic Compliant Citric Acid
Organic Turmeric Root Powder
Organic Fennel Seed Powder
Organic Ginger Root In one embodiment, these are combined in a ratio of 1:0.8-1.0:0.55-0.65:0.40-0.54:0.05-0.09:0.05-0.09.

Preservative Blend 2
Organic Cultured Dextrose
Organic Elderberry (16:1 Fruit Powder)
Organic Compliant Citric Acid
Organic Echinacea Purpurea Herb (6:1)

In one embodiment, these are combined in a ratio of 1:0.60-0.70:0.55-0.65:0.35-0.44.

The blend is used at 2-5% w/w of the final formulation. As evidenced by the USP testing disclosed herein, formulations utilizing this stability system have demonstrated stability.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

What is claimed:

1. A liquid composition comprising:
    a) a primary component that is a base of a nutritional supplement; and
    b) a preservative blend comprising
        i) Organic Dextrose,
        ii) Organic Elderberry (16:1 Fruit Powder),
        iii) Organic Citric Acid,
        iv) Organic Turmeric Root Powder,
        v) Organic Fennel Seed Powder, and
        vi) Organic Ginger Root, wherein the ratios of components (i)-(vi) are 1:0.8-1.0:0.55-0.65:0.40-0.54:0.05-0.09:0.05-0.09.

2. The composition of claim 1 wherein the preservative blend is 2-5% w/w of the composition.

3. A method of preparing the liquid composition of claim 1, comprising the steps of:
    a) providing the components of the preservative blend, wherein the components are:
        i) Organic Dextrose,
        ii) Organic Elderberry (16:1 Fruit Powder),
        iii) Organic Citric Acid,
        iv) Organic Turmeric Root Powder,
        v) Organic Fennel Seed Powder, and
        vi) Organic Ginger Root,
    b) combing them into an herbal pre-mix;
    c) blending them into the base;
    d) heating the mixture made in step (c) between 180 and 200 degrees Fahrenheit, to create a second pre-mix containing the herbal ingredients;
    e) combining the second pre-mix with a mixture of agave and honey, which has been heated to about 100° F. and mixing until the second pre-mix and the mixture of agave and honey are homogenous and become one product;
    f) cooling the mixture made in step (e) to room temperature;
    g) introducing flavors at room temperature; and
    h) mixing the composition made in step (g) to form a uniform composition.

* * * * *